(12) United States Patent
Griffard et al.

(10) Patent No.: US 10,307,728 B1
(45) Date of Patent: Jun. 4, 2019

(54) HIGH REACTIVITY LIME HYDRATE AND METHODS OF MANUFACTURING AND USES THEREOF

(71) Applicant: MISSISSIPPI LIME COMPANY, St. Louis, MO (US)

(72) Inventors: Randy J. Griffard, St. Mary, MO (US); Mark G. Degenova, St. Genevieve, MO (US); Stephen C. Schweigert, St. Genevieve, MO (US); Gerald K. Bequette, St. Genevieve, MO (US); William S. Allebach, St. Genevieve, MO (US); Zhichao Richard Zhang, Chesterfield, MO (US); Curtiss R. Biehn, O'Fallon, IL (US)

(73) Assignee: Mississippi Lime Company, St. Louis, MO (US)

( * ) Notice: Subject to any disclaimer, the term of this patent is extended or adjusted under 35 U.S.C. 154(b) by 137 days.

(21) Appl. No.: 15/344,173

(22) Filed: Nov. 4, 2016

Related U.S. Application Data

(62) Division of application No. 13/594,538, filed on Aug. 24, 2012, now Pat. No. 9,517,471.

(60) Provisional application No. 61/528,015, filed on Aug. 26, 2011, provisional application No. 61/528,012, filed on Aug. 26, 2011, provisional application No. 61/528,023, filed on Aug. 26, 2011.

(51) Int. Cl.
| | | |
|---|---|---|
| *B01D 53/46* | (2006.01) | |
| *B01J 20/04* | (2006.01) | |
| *B02C 23/10* | (2006.01) | |
| *B02C 23/12* | (2006.01) | |
| *G01N 21/80* | (2006.01) | |
| *B01D 53/50* | (2006.01) | |
| *B01D 53/83* | (2006.01) | |
| *C01F 11/02* | (2006.01) | |
| *C04B 2/04* | (2006.01) | |

(52) U.S. Cl.
CPC .......... *B01J 20/041* (2013.01); *B01D 53/508* (2013.01); *B01D 53/83* (2013.01); *B02C 23/10* (2013.01); *B02C 23/12* (2013.01); *C01F 11/02* (2013.01); *C04B 2/045* (2013.01); *G01N 21/80* (2013.01); *B01D 2251/404* (2013.01); *B01D 2251/604* (2013.01); *B01D 2253/10* (2013.01); *B01D 2253/304* (2013.01); *B01D 2253/306* (2013.01); *B01D 2253/311* (2013.01); *B01D 2257/302* (2013.01)

(58) Field of Classification Search
CPC .................................................. B01D 53/508
See application file for complete search history.

(56) References Cited

U.S. PATENT DOCUMENTS

| | | |
|---|---|---|
| 309,328 A | 12/1884 | Adams |
| 671,621 A | 4/1901 | Dodge |
| 1,613,341 A | 1/1927 | Carson |
| 1,679,149 A | 7/1928 | Berg |
| 1,954,211 A | 4/1934 | Kuntz |
| 2,894,820 A | 7/1959 | Rikard et al. |
| 3,366,450 A | 1/1968 | Waldeck |
| 3,839,551 A | 10/1974 | Dozsa et al. |
| 3,929,417 A | 12/1975 | Rosa et al. |
| 4,330,514 A | 5/1982 | Nagai et al. |
| 4,636,379 A | 1/1987 | Bestek et al. |
| 5,173,279 A | 12/1992 | Dumont et al. |
| 5,223,239 A | 6/1993 | Moran et al. |
| 5,277,837 A | 1/1994 | Dumont et al. |
| 5,332,436 A | 7/1994 | Walker, Jr. et al. |
| 5,705,141 A | 1/1998 | Dumont et al. |
| 5,935,299 A * | 8/1999 | Park ............... B01D 47/06 |
| | | 261/116 |
| 6,200,543 B1 | 3/2001 | Allebach et al. |
| 6,322,769 B1 | 11/2001 | Langelin et al. |
| 7,338,649 B2 | 3/2008 | Huege et al. |
| 7,744,678 B2 | 6/2010 | Laudet et al. |
| 2007/0082978 A1 | 4/2007 | Suzuki et al. |
| 2009/0229462 A1 | 9/2009 | Laudet et al. |
| 2009/0246117 A1 | 10/2009 | Tilquin et al. |
| 2009/0246524 A1 | 10/2009 | Ohmi et al. |
| 2011/0150755 A1 | 6/2011 | Euston |

FOREIGN PATENT DOCUMENTS

| | | |
|---|---|---|
| GB | 1394330 | 5/1975 |
| JP | 2007031212 A | 2/2007 |

OTHER PUBLICATIONS

Nolan, Paul S. and Brinker, Michael R., "Hydrated Lime for Control of Acid Gas Emissions from Coal-Fired Power Plants," 12 pages.
Gale, Thomas K., Cannon, Jared W, Nolan, Paul S., Brinker, Michael R., Brasseur, Alain and Laudet, Alain, "Hydrated Lime for SO3 Removal," Paper #128, 16 pages.
Srivastava, R.K., Miller, C.A., Erickson, C. and Jambhekar, R., "Emissions of Sulfur Trioxide From Coal-Fired Power Plants," Technical Publication, Riley Power Inc, a Babcock Power Inc. company, www.babbockpowercom, presented at POWER-GEN International 2002, Dec. 10-12, 2002, Orlando, Florida, 20 pages.
"A Guidebook to Particle Size Analysis," Horiba Scientific, pp. 1-29, 17 pages.

(Continued)

*Primary Examiner* — Paul S Hyun
(74) *Attorney, Agent, or Firm* — Lewis Rice LLC

(57) ABSTRACT

A sorbent composition with improved acid gas reactivity comprising calcium hydroxide particles is provided. In the calcium hydroxide composition, about 90% percent of the calcium hydroxide particles are less than or equal to about 10 microns; the ratio of 90% of the calcium hydroxide particles below a specified size to the ratio of 10% of the calcium hydroxide particles above a specified size is less than about 8; and the calcium hydroxide particles have a BET surface area of about 18 $m^2/g$ or greater.

6 Claims, 9 Drawing Sheets

(56) References Cited

OTHER PUBLICATIONS

Peterson, Joseph R., Mailer, Gordon, Burnette, Andrew and Rhudy, Richard G., "Pilot-Scal Evaluation of Sorbent Injection to Remove SO3 and HCL," Managing Hazardous Air Pollutants State of the Art, Electric Power Research Institute TR-101890, printed Nov. 16, 2009, pp. 520-538, 22 pages.

* cited by examiner

HIGH REACTIVITY LIME HYDRATE AND METHODS OF MANUFACTURING AND USES THEREOF

CROSS REFERENCE TO RELATED APPLICATION(S)

This Application is a Divisional of U.S. Utility patent application Ser. No. 13/594,538, filed Aug. 24, 2012 and currently pending, which in turn claims the benefit of U.S. Provisional Patent Application Ser. Nos. 61/528,023, filed Aug. 26, 2011; 61/528,015, filed Aug. 26, 2011; and 61/528,012, filed Aug. 26, 2011. The entire disclosure of all the above references is incorporated by reference herein.

BACKGROUND OF THE INVENTION

1. Field of the Invention

This disclosure is related to the field of quicklime products and methods of manufacturing and uses thereof, specifically to compositions and methods of manufacturing and uses of compositions comprising calcium hydroxide—more commonly called hydrated lime or lime hydrate—that have quick reactivity with acids and specifically acid gases and halogenated acid gases such as sulfur trioxide.

2. Description of Related Art

Many efforts have been made to develop materials for improved capability of cleaning or "scrubbing" flue gas or combustion exhaust. Most of the interest in such scrubbing of flue gas is to eliminate particular compositions, specifically acid gases, that provide particularly detrimental known environmental effects, such as acid rain.

Flue gases are generally very complex chemical mixtures which comprise a number of different compositions in different percentages depending on the material being combusted, the type of combustion being performed, impurities present in the combustion process, and specifics of the flue design. However, certain chemicals which commonly appear in flue gases are known to be undesirable to have exhausted, and therefore their release is generally regulated by governments and controlled by those who perform the combustion.

Some such materials that are subject to regulation are certain acid gases. A large number of acid gases are desired to be, and are, under controlled emission standards in the United States and other countries. This includes compounds such as, but not limited to, hydrogen chloride (HCl), sulfur dioxide ($SO_2$) and sulfur trioxide ($SO_3$). Sulfur trioxide can evidence itself as condensable particulate in the form of sulfuric acid ($H_2SO_4$). Condensable particulate can also be a regulated emission. Flue gas exhaust mitigation is generally performed by devices called "scrubbers" that provide additional chemical compounds into the flue gas that react with the compounds to be removed either allowing them to be captured and disposed of, or allowing them to be reacted into a less harmful compounds prior to their exhaust, or both. In addition to control for environmental reasons, it is desirable for many combustion plant operators to remove acid gases from their flue gas to prevent them from forming powerful corroding compounds which can damage their flues and other equipment.

These acid gases can arise from a number of different combustion materials, but are fairly common in fossil fuel combustion (such as oil or coal) due to sulfur being present as a common contaminant in the raw fuel. Most fossil fuels contain some quantity of sulfur. During combustion, sulfur in the fuel can oxidize to form sulfur oxides. A majority is sulfur dioxide ($SO_2$) but a small amount of sulfur trioxide ($SO_3$) is also formed. Selective Catalyst Reduction (SCR) equipment, commonly installed for removal of nitrogen oxides ($NO_x$) will also oxidize a portion of the $SO_2$ in flue gas to $SO_3$. Other components of the process (iron, etc.) can increase the amount of $SO_3$ that forms in the flue gas. Particularly in coal combustion, where the chemical properties of the coal are often highly dependent on where it is mined, the ability to mitigate the amount of sulfur oxides in flue gas is highly desirable as it allows for lower quality raw coal (which may be less expensive to produce and more abundant) to be burned sufficiently cleanly to lessen environmental impact and impact on machinery.

$SO_2$ is a gas that contributes to acid rain and regional haze. Since the 1970's, clean air regulations have reduced emissions of $SO_2$ from industrial processes at great benefit to the environment and human health. For large emitters, the use of wet and dry scrubbing has led to the reduction of $SO_2$. Smaller emitters, however, require less costly capital investment to control $SO_2$ emissions to remain operating in order to produce electricity or steam.

Similarly, halides in fossil fuels (Cl and F) are combusted and form their corresponding acid in the flue gas emissions. The halogenated acids also contribute to corrosion of internal equipment or, uncaptured, pollute the air via stack emissions.

Mitigation, however, can be very difficult. Because of the required throughput of a power generation facility, flue gases often move through the flue very fast and are present in the area of scrubbers for only a short period of time. Further, many scrubbing materials often present their own problems. Specifically, having too much of the scrubbing material could cause problems with the plant's operation from the scrubber material clogging other components or building up of moving parts.

Some removal of $SO_3$ occurs within the system. FIG. 1 shows an embodiment of a flue system. As flue gas cools in the Air Preheater (APH), a portion of the $SO_3$ can deposit on the internals of the equipment. The presence of a small amount of $SO_3$ lowers the resistivity of fly ash and is generally beneficial towards capture of ash in an electrostatic precipitator. Additional $SO_3$ can be removed by absorption onto the fly ash in the flue or the particulate collection device.

A majority of the $SO_3$, however, passes through the system unchecked. Remaining $SO_3$ that continues through the APH can pass through dew point and form a sulfuric acid mist. This mist continues through the post-APH ductwork and particulate collection device. Plants equipped with a wet Flue Gas Desulfurization (FGD) system will form $H_2SO_4$ aerosols as the flue gas is quenched in the scrubber. This action results in a characteristic blue plume emitted from the stack.

The presence of $SO_3/H_2SO_4$ in flue gas necessitates a variety of operation considerations. Use of wet flue gas desulfurization for $SO_2$ control can generate a tell-tale blue plume of sulfuric acid mist that is an eyesore at best and environmental risk to the local community at worst. The primary risk of a blue plume is a touch down into neighboring areas, causing potential health effects, corrosion of property, damage to vegetation, and/or potential negative attention due to the appearance of the stack emission.

Corrosion of process equipment is also a risk. Equipment that can be affected includes duct work, fans (Air Preheater), and the internals of particulate collection devices. Process temperatures for heat recovery are dictated by acid dew point temperature of the flue gas. Ammonia slip from SCR operation can react with $SO_3$ to form ammonium bisulfate (ABS), a sticky precipitate that clogs air heater internals.

The presence of acid gases in flue gas dictates operational decisions and increases operating costs. Minimization of $SO_2$ conversion to $SO_3$ may warrant the extra expense of low conversion catalyst in a SCR. Fear of forming sticky ammonium bisulfate (ABS) particles on APH internals will affect operation of the SCR in order to contain ammonia slip. The need to operate safely above dew point in the APH increases heat rate and resulting energy costs. Greater air flow due to a high heat rate translates to additional power required to run the fans. Ash release from baghouse bags can be less efficient if the acid gases are untreated. Units equipped with wet FGD will remove HCl, but the chlorides in the wet system can lead to corrosion issues or additional processing in water treatment.

Many coal-fired power plants are also faced with regulations on mercury emissions. $SO_3$ in flue gas absorbs onto activated carbon—a common sorbent used for capture of mercury emissions—thereby lowering its ability to capture mercury. Units utilizing bituminous coal must remove $SO_3$ before treating with activated carbon, thus the ability to remove $SO_3$ to very low levels is necessary for units facing mercury removal requirements. There are high capital cost options such as Wet ESPs available, but those may not be capable of reducing high levels of $SO_3$. In addition, a Wet ESP does not offer any upstream corrosion prevention.

Flue gas treatment has become a focus of electric utilities and industrial operations due to increasingly tighter air quality standards. As companies seek to comply with air quality regulations using cost-effective fuels, the need arises for effective flue gas treatment options. Alkali species based on alkali or alkaline earth metals are common sorbents used to neutralize the acid components of the flue gas. The most common of these alkalis are sodium, calcium, or magnesium-based. A common method of introduction of the sorbents into the gas stream is to use Dry Sorbent Injections. The sorbents are prepared as a fine or coarse powder and transported and stored at the use site. Dry sorbent injection systems pneumatically convey powdered sorbents to form a fine powder dispersion in the duct. The dry sorbent neutralizes $SO_3/H_2SO_4$, and protects equipment from corrosion while eliminating acid gas emissions. Common sorbents used are sodium (trona or sodium bicarbonate) or calcium (hydrated lime, $Ca(OH)_2$) based.

One proposed material for use in scrubbing of acid gases is increased use of hydrated lime. It has been established that hydrated lime can provide a desirable reaction to act as a mitigation agent.

Hydrated lime reacts with $SO_3$ to form calcium sulfate in accordance with the following equation:

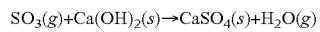

$$SO_3(g)+Ca(OH)_2(s)\rightarrow CaSO_4(s)+H_2O(g)$$

Hydrated lime systems are proven successful in many full scale operations. These systems operate continuously to provide Utility companies with a dependable, cost-effective means of acid gas control.

The most effective hydrated lime sorbents for Dry Sorbent Injection have high (>20 $m^2/g$) BET surface area. Two examples of such compositions with increased BET surface areas are described in U.S. Pat. Nos. 5,492,685 and 7,744,678, the entire disclosures of which are herein incorporated by reference. These sorbents offer good conveying characteristics and good dispersion in the flue gas, which is necessary for high removal rates. Use of a higher quality, high reactivity source of hydrated lime allows for better stoichiometric ratios than previous attempts that utilized lower quality hydrated lime originally targeted for other industries such as wastewater treatment, construction, asphalt, etc. Hydrated lime is versatile in terms of injection location; removal of $SO_3$ will occur with injection prior to SCR, prior to the Air Preheater (APH), post (APH) injection, post particulate collection injection, or any combination of these.

Removal of $SO_3$ by a sorbent is dictated by the ability of the sorbent to contact the acid gas prior to entering the particulate collection device. The use of multiple injection sources to improve $SO_3$ capture is an option. Sizing of the particulate collection device and ability to control the expected additional solids loading due to sorbent injection should also be examined.

These compositions specifically focus on high surface area based on the theories of Stephen Brunauer, Paul Hugh Emmett, and Edward Teller (commonly called BET theory and discussed in S. Brunauer, P. H. Emmett and E. Teller, J. Am. Chem. Soc., 1938, 60, 309, the entire disclosure of which is herein incorporated by reference). This methodology particularly focuses on the available surface area of a solid for absorbing gases—recognizing that a surface, in such circumstances, can be increased by the presence of pores and related structures. The reaction of hydrated lime with acid gas (such as $SO_3$) is generally assumed to follow the diffusion mechanism. The acid gas removal is the diffusion of $SO_3$ from the bulk gas to the sorbent particles. High surface area does not itself warrant a prediction in improved removals of acid gases. Specifically, high pore volume of large pores is generally believed to be required to minimize the pore plugging effect and, therefore, BET surface area has been determined to be a reasonable proxy for effectiveness of lime hydrates in removal of acid gases.

Because of this, commercially available products are currently focused on obtaining lime hydrate with particularly high BET surface areas. It is generally believed that the BET surface area really needs to be above 20 $m^2/g$ to be effective, and in many recent hydrated lime compositions the BET surface area is above 30 $m^2/g$ to attempt to continue to improve efficiency.

Much of the efficiency of Dry Sorbent Injection is dictated by the ability of the injection system to have the sorbent contact the acidic components of the flue gas. Flue gas pathways are not homogeneous in nature, as structural components of the flue, wall effects, and combustion processes provide a flue gas stream that can be stratified horizontally or vertically. It is the job of the DSI system to put the sorbent where the acid gas travels. Sorbent which does not enter the zones where acid is concentrated is free to react with other components of the flue gas or remain unreacted until removed in particulate collection or FGD Systems with short residence time (<2 sec) prior to particulate collection. FGD Systems are particularly vulnerable to reactivity issues related to the inability to fully disperse hydrated lime sorbent throughout the flue gas in the short length of flue available.

Due to dispersion inefficiencies in the flue gas, sorbents are typically added at concentrations in excess of the acid gas to be neutralized. Depending upon the flue configuration and sorbent injection system, the amount of hydrated lime to $SO_3$ can be 1-4 moles of hydrate:mol of $SO_3$. More challenging systems will require a treat rate as high as 5-10 moles of hydrate:mol of $SO_3$. The excess required presents the end user with an economic disadvantage.

Further, most current Utilities that require acid gas mitigation utilize an Electrostatic Precipitator (ESP). This equipment uses electrostatic charges to drive ash in the flue gas against charged metal plates. Ash collects on the plates and then is removed (rapping) at regular intervals. ESP sizing will determine the amount of ash that can be removed. Excessive amounts of ash beyond the ESPs capacity will lead to problems with opacity limits. These limits are commonly regulated, typically ~20% maximum opacity. Some units may also be regulated for particulate emissions. Too much ash will lead to increased particulate emissions.

Many existing ESPs were sized based upon the expected ash from the coal being used to fire the boiler. The ESPs were designed and installed prior to dry sorbent injection, so the added particulate as the result of DSI was not factored into ESP capacity. Units with undersized ESPs that have a relatively high amount of $SO_3$ present in the flue gas can encounter operational problems due to the addition of hydrated lime sorbent injection. In some configurations, calcium reagents may increase the resistivity of the ash that collects on the ESP plates. If the resistivity is increased too much, the ESP plates will not capture ash from the flue gas, resulting in increased opacity and particulate content of the flue gas exiting the ESP. The extra particulate may not be captured in a downstream scrubber, leading to emission problems with the unit. The resistivity problem can occur with a small amount of hydrate if the ESP is marginally sized for the ash loading. If the acid gas content of the flue gas is relatively high, the amount of sorbent required to capture acid gas prior to ESP may be so high as to cause resistivity issues with an ESP even of moderate size.

Alkali sodium sorbents decrease the resistivity ash and, in some cases, may actually aid an undersized ESP. Because of the resistivity issues with ash, hydrated lime sorbents can be at a competitive disadvantage on units having high $SO_3$ content and/or an undersized ESP for the expected ash loading.

While higher BET hydrated limes have proven effective at certain forms of scrubbing, pilot-scale evaluation of sorbent injection for removing acid gases (i.e. $SO_3$ and HCl) showed that the high surface area hydrated lime performed no better than commercial grade hydrated lime. [Peterson, J. R., Mailer, G., Burnette, A. and Rhudy. In Managing Hazardous Air Pollutants (Eds W. Chow and K. K. Connor, EPRI), 1993, pp 520-538 which is incorporated herein by reference]. The diffusion model proposed above, however, shows the removal rate is strongly dependent on injection rate, residence time, and the average diameter of sorbent particles.

While this analysis would indicate that smaller particles are better, sizes of the particles of hydrated lime as well as other sorbents can be produced to smaller sizes simply by increased or improved milling. However, the particle size distribution about the average generally depends on the manufacturing processes used to produce them and, therefore, compositions with identical averages can have different size distributions.

SUMMARY

Because of these and other problems in the art, described herein, among other things, is a sorbent composition with improved acid gas reactivity comprising calcium hydroxide particles. In this composition, 90% percent of the particles are less than or equal to about 10 microns; the ratio of 90% of the particles below a specified size to the ratio of 10% of the particles below a specified size is less than about 8; and the particles have a BET surface area of about 18 $m^2/g$ or greater.

In some embodiments, the ratio of 90% of the particles below a specified size to the ratio of 10% of the particles below a specified size is less than about 6. In other embodiments, the ratio is between about 4 and about 7. In still other embodiments, the ratio is between about 5 and about 6.

In another embodiment, 90% percent of the particles are less than or equal to about 8 microns. Alternatively, 90% percent of the particles are less than or equal to about 6 microns. 90% percent of the particles also can be between about 6 microns and about 4 microns or between about 5 microns and about 4 microns.

In some embodiments, the particles have a BET surface area of about 20 $m^2/g$ or greater. The composition also may comprise at least about 95% calcium hydroxide particles.

Also disclosed herein is a sorbent composition with improved acid gas reactivity comprising: calcium hydroxide particles having a reactivity of less than 10 seconds. The reactivity is the amount of time it takes the calcium hydroxide particles to neutralize in citric acid with the citric acid having a mass greater than 10 times the mass of the calcium hydroxide particles.

In some embodiments, the reactivity is less than about 8 seconds. In others, the reactivity is about 4 seconds or less. In still others, the reactivity is about 3 seconds or less. In yet another embodiment, the reactivity is between about 2 seconds and about 5 seconds.

The calcium hydroxide particles also may have a mass of about 1.7 grams and the citric acid may have a mass of about 26 grams. In some of these embodiments, the reactivity is less than about 8 seconds. In other of these embodiments, the reactivity is about 4 seconds or less. In still others, the reactivity is about 3 seconds or less. In yet another one of these embodiments, the reactivity is between about 2 seconds and about 5 seconds.

In some embodiments, the citric acid has a mass greater than 15 times the mass of the calcium hydroxide particles. In other embodiments, the composition comprises at least about 95% calcium hydroxide particles.

Also disclosed herein is a sorbent composition with improved acid gas reactivity consisting essentially of: calcium hydroxide particles having a reactivity of less than 10 seconds. In such embodiment, the reactivity is the amount of time it takes the calcium hydroxide particles to neutralize in citric acid, the citric acid having a mass greater than 10 times the mass of the calcium hydroxide particles.

DETAILED DESCRIPTION OF PREFERRED EMBODIMENTS

Figure 1:
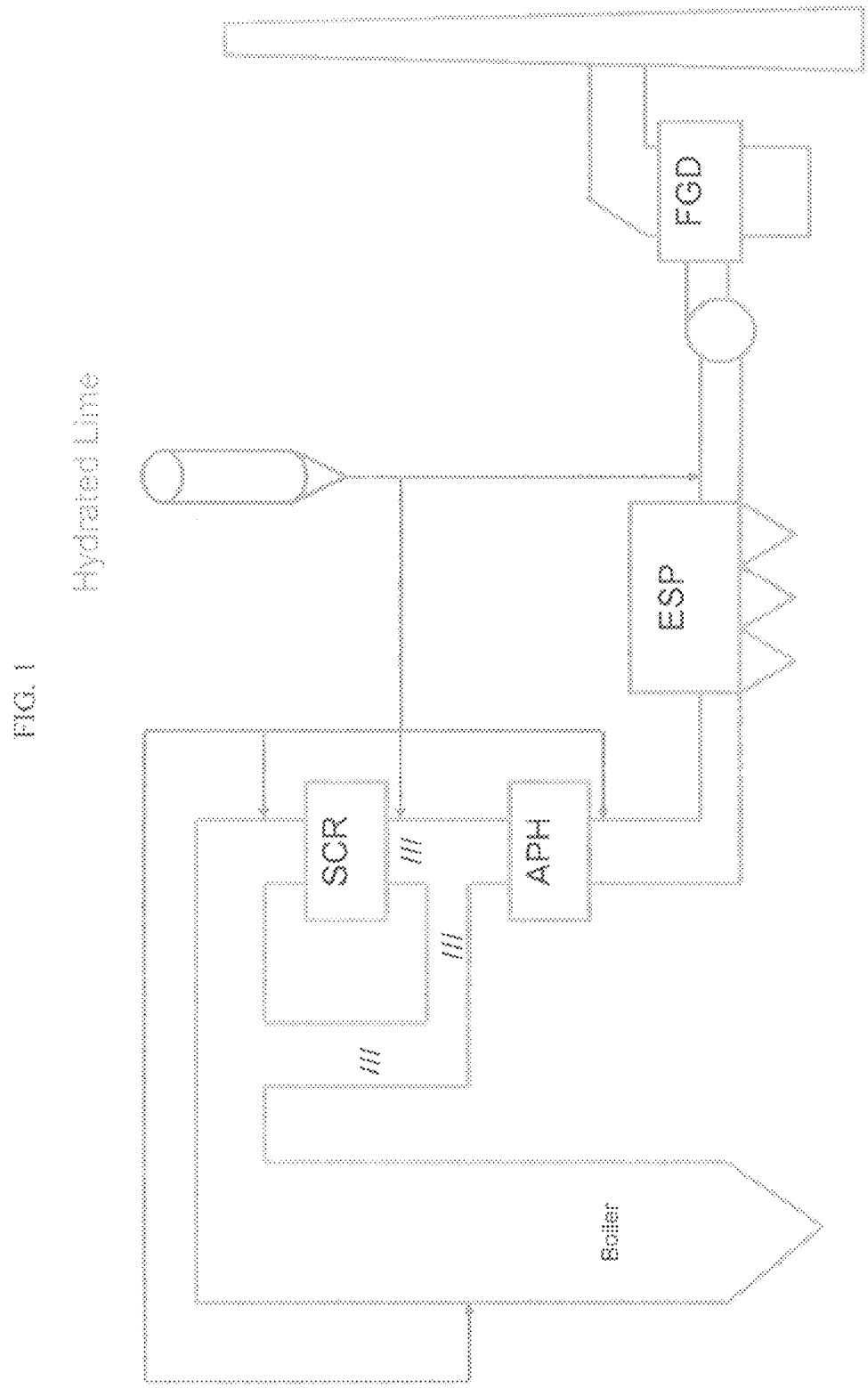
FIG. 1 provides a block diagram of a flue system common in a coal fired power plant indicating where hydrated lime may be injected to reduce acid gases.

There is described herein a lime hydrate composition—end methods of manufacturing and uses of the same—designed for improved acid gas reactivity by providing that the composition has a high surface area, while it is also provided with a smaller average particle size, and specifically also has a narrow band of particle sizes. This last quality is generally referred to as its steepness. What has been found is that particles having a steep size distribution, even with lower BET surface area values and higher average particle sizes, can still outperform products that would have traditionally been indicated to be better due to smaller average particle size and higher BET surface area. Further, if the average particle size and BET surface area remain constant, while the size distribution is increased in steepness (a narrower size band), the reactivity of the composition improves.

More specifically, the methods disclosed herein can produce a high reactivity lime hydrate composition, which has a BET surface area of 18 $m^2/g$ or greater, a d90 particle size of 10 microns or smaller, and a d90/d10 ratio of 8 or less. Alternatively, high reactive lime hydrates can be identified by their reaction time when acting on citric acid of approximately 10 times mass. In this case, the reaction time is generally 10 seconds or less, but may be 8 seconds or less in another embodiment.

With regards to the particle size and distribution, the composition generally will include particles which are of various sizes, as compositions of particles of only one size are effectively impossible to obtain without massive cost and using current techniques. While in an embodiment, compositions with homogenous or nearly homogenous particle size are contemplated, these compositions are generally overly expensive to produce and are not currently commercially viable. Instead, this disclosure contemplates reducing three variables of the composition (surface area, average particle size, and particle size distribution).

As contemplated above BET surface area is used and, in an embodiment, the compositions will comprise a BET of 18 $m^2/g$ or better. In order to provide for specifics as to average particle size and distribution, the following measurements are used herein to discuss the particle size and steepness of distribution. Specifically, this disclosure will use the standard particle size evaluations of d90 and d10. A d90 size indicates that 90% of the material is below the specified size. Similarly, d10 indicates that 10% of the material is under the specified size. In the present disclosure, it has been found that compositions with a d90 below about 10 microns, and in an embodiment below about 6 microns, and the ratio of d90/d10 being less than about 8 produces a lime hydrate composition which shows much greater acid reactivity than other lime hydrates. Sizes were determined using a Helos™ particle size analyzer. These are termed "high reactive" lime hydrates in this disclosure based on their reactivity with citric acid, as discussed later.

Further, while the above refers to specifics of the lime hydrate in composition, it is recognized that in the formation of lime hydrates, the composition will generally include other materials comprising contaminants or waste. These do not have any effect on the ability of the composition to react with the acid gas, but can, however, result in the composition having too little calcium hydroxide ($Ca(OH)_2$) to act as a scrubber when injected in commercially reasonable amounts. Thus, in discussing the lime hydrate compositions of the present disclosure, it is preferred that the composition comprise at least 95% calcium hydroxide (by weight)—with the composition, taken as a whole, meeting the above size criteria. This is, however, not required and in alternative embodiments the lime hydrate composition consists of calcium hydroxide with no contaminants present (a pure form) or the lime hydrate consists essentially of calcium hydroxide where other materials present in the composition are generally considered non-reactive with acid gases or provides no substantive acid gas removal. In the latter case, the resultant composition would be used in the scrubber in sufficient quantities that the total amount of calcium hydroxide is sufficient to react as would be desired by one of ordinary skill in the art.

In one embodiment of manufacturing, the high reactive lime hydrate is produced utilizing the 95% criterion. Specifically, in this method, a compound is produced where certain values of calcium hydroxide is not known, if the compound is reduced to be in the steepness range discussed above, the compound has been found to generally include 95% or more calcium hydroxide. In effect, the steepness and total size criteria serve as an indicator that sufficient contaminants have been removed from the composition (which are often outside the narrow band dictated by the steepness) to produce the desired composition.

The 95% criterion is not absolute as lower percentage inclusion of calcium hydroxide in the composition can be mitigated by simply using more of it. However, the 95% composition can provide for another check on the steepness of the distribution of the calcium hydroxide and composition. Specifically, if a compound is produced where the ratio of calcium hydroxide is not known, and if the compound is reduced to be in the steepness range discussed above, the compound has been found to generally include 95% or more calcium hydroxide. In effect, the steepness and total size criteria serve not only to improve the reactivity of the calcium hydroxide portion of the lime hydrate composition, but also can serve to eliminate contaminants from the composition (which are often outside the narrow band dictated by the steepness), thereby improving the commercial viability of the composition.

While it is believed that particles and distributions equal to or smaller than the above will provide for effective mitigation, it is recognized that general reductions in particle size, including d90 particle size values of about 8 microns or less, about 6 microns or less, about 5 microns or less, about 4 microns or less, about 3 microns or less, about 2 microns or less, about 1 micron or less, or about 0.1 micron or less can result in an increasingly active compound so long as the other two criteria also remain in the range. It should be recognized that too much of a reduction in particle size may very well result in a reduction of BET for the material as, eventually, the smallness of the particle may result in the structural characteristics of the particles being destroyed and that such reductions generally require significantly increased costs from additional milling. Therefore, it is generally the case that d90 particle size will be between 6 microns and 4 microns and more preferably between about 5 microns and about 4 microns. However, reductions of d90 to these lower levels are generally not effective in acid gas mitigation unless the d90/d10 ratio remains under about 8.

Figure 8:
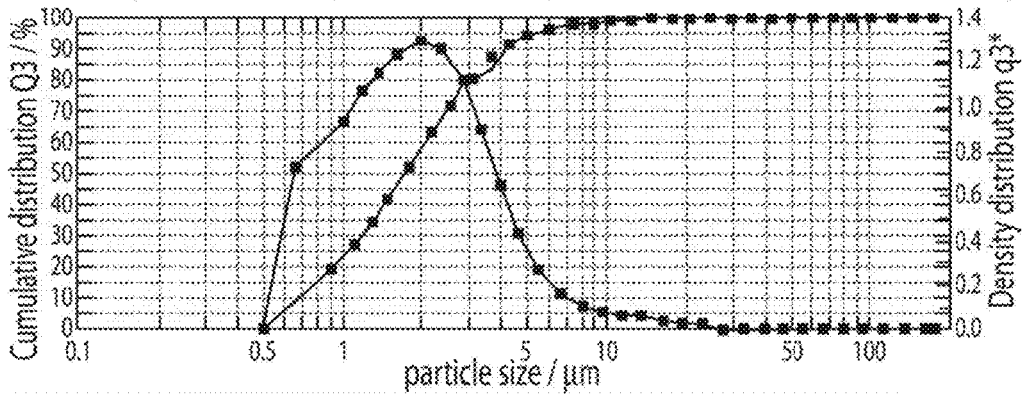
FIG. 8 provides a detailed particle size analysis of an embodiment of a high reactive lime hydrate.

Similarly, d90/d10 ratios of under about 7, under about 6, under about 5, under about 4, under about 3, or under about 2 also generally provide improved reactivity so long as the other two variables also are maintained in the above ranges. It should be recognized that producing extremely narrow bands of material (ideally producing those with a ratio of 1 which are near homogenous) can result in significantly increased processing. Therefore, in the interest of current manufacturing techniques, in an embodiment the ratio of d90/d10 will be between about 4 and about 7 or alternatively may be between about 5 and about 6. FIG. 8 shows a detailed particle size analysis of an embodiment of a lime hydrate composition of the present invention.

Figure 7:
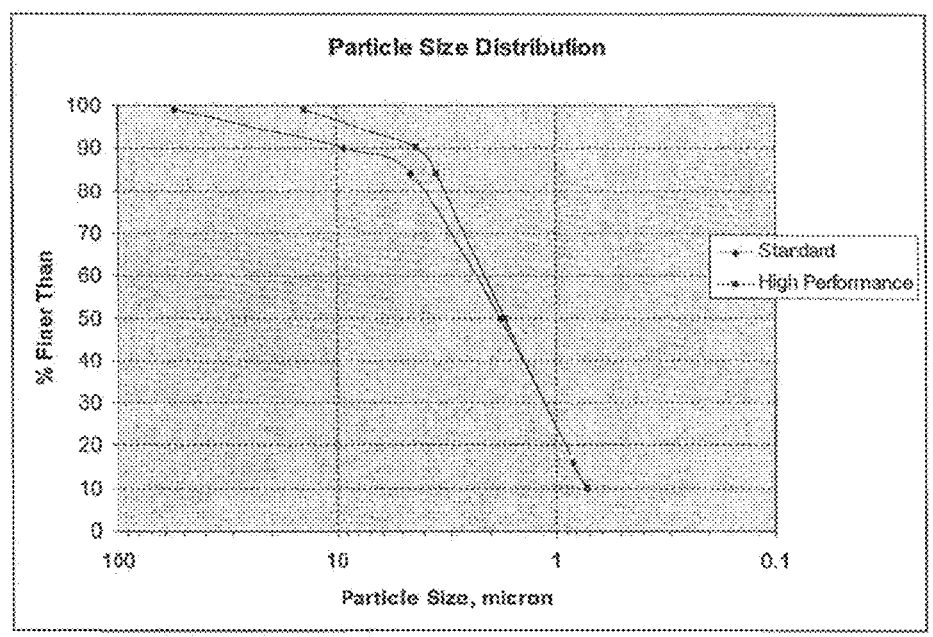
FIG. 7 provides a graph showing the relative percentage of particles at particular particle sizes in a standard and a high reactivity hydrate having generally the same average particle size.

The narrow particle size distribution of the lime hydrate composition may be also reflected in its low content of oversized materials. Specifically, other ratios (not just d90/d10) may be used to show that a relatively narrow band of materials exist. For example, the ratio d90/d50 may alternatively be used, or the standard deviation from the mean may be used. Further, the use of d90 for a particle size is not required. Alternatively, other particle size calculations such as d50 (mean) size may be used. In an embodiment the d50 value will generally be less than 4 microns, preferably less than 2 microns and, simply due to constraints on manufacturing techniques, may in an embodiment be between 2 and 1 microns. FIG. 7 shows an embodiment comparing the relative particles sizes as calculated at different percentage values to show the narrower band present in a high reactive hydrate. As would be understood to one of ordinary skill in the art, products with similar d90/d10 ratios will also generally have similar d90/d50 ratios and therefore the above three calculations (BET surface area, d90, and d90/d10) provide an effective way to determine compositions which are highly reactive.

The development of a high purity hydrated lime with a narrow, small particle size distribution improves dispersion in the flue gas when the sorbent is delivered to the process. The finer cloud from the sorbent injection lance puts more sorbent particles in the pathway of acid gases, reaching stratified areas and neutralizing more acid components.

The development of a hydrated lime that is more reactive can allow a utility to use calcium reagents for acid gas mitigation where before the unit's ESP limited them to only sodium sorbents. The benefits to the utility can be significant and can include flexibility in sourcing to allow more competitive pricing, and the ability to eliminate sodium salts from their ash. Sodium salts will cause issues with leaching in landfills while calcium salts will not leach.

More reactive hydrated lime also allows the end user to feed less sorbent to achieve the same acid gas removal. The reduced loading on the particulate collection device should benefit operation. A more reactive hydrate allows use in units with a short residence time prior to the particulate collection device. If the site has to reduce acid gas to a predetermined level, a more reactive hydrate requires 10-30% less sorbent. In many cases, units have to feed a stoichiometric ratio well beyond equimolar (1 mol hydrated lime:1 mol $SO_3$) or even industry typical (1-4 mol hydrated lime:1 mol $SO_3$); as much as 5-10 mol hydrated lime:1 mol $SO_3$. A hydrate that is able to more effectively capture acid gas in a short span will reduce ash loading on the ESP.

Additionally, process benefits can be recognized from the use of higher reactive hydrated lime. Processes may have equipment constraints where acid gas pollutants must be removed within a relatively short period of time (residence time). FIG. 1 provides for an embodiment of location at which lime hydrate could be injected into the system. Examples could include, but not limited to:

Injection of sorbent to remove $SO_3$ prior to an Air Preheater in order to recapture more heated air for combustion in the boiler.

Injection of sorbent to remove $SO_3$ prior to an Air Preheater in order to eliminate issues caused by reaction of $SO_3$ with other components of the flue gas which produce a byproduct detrimental to operation of the Air Preheater. An example is the reaction of $SO_3$ with NH3 emitted from $NO_x$ pollution control equipment for form ammonium bisulfate (ABS). ABS is a sticky solid that will deposit on APH internals, often fouling them to the point that the equipment must be taken offline and cleaned.

Co-injection of a sorbent to remove other pollutants present in the flue gas. One example is the injection of carbon species to remove mercury. $SO_3$ can deposit on the carbon species and render it inactive towards mercury absorption. Removal of $SO_3$ prior to injection of the carbon species is necessary to maintain acceptable mercury sorbent usage levels. Often, site equipment constraints limit the potential injection locations for the Acid Gas and Mercury sorbents.

Process layout constraints where the only suitable injection location for acid gas sorbent is within a short (<2 sec) residence time of particulate collection or wet desulfurization processes.

Injection of hydrated lime prior to the Selective Catalyst Reduction equipment for mitigation of SO3. Especially during periods of reduced load, control of SO3 that is generated in the boiler may be beneficial to the unit with regard to emissions and/or minimum operating temperature and it resultant effect on minimum load on the unit.

Injection of hydrated lime prior to the Selective Catalyst Reduction equipment for mitigation of arsenic species that are catalyst poisons. Arsenic present in coal can infect catalyst layers and reduce efficiency of the NOx removal process. Reaction of arsenic oxides with calcium reagents forms calcium aresenates, which are not catalyst poisons.

HCl removal: Regulations typically demand reduction of HCl to very low levels (2015 Utility MACT, 0.002 lb/mmBtu). Mechanistically, HCl is mitigated after elimination of most SO3 in the flue gas. A more reactive hydrate offers the end user the benefit of removing more acidic species than may be capable with standard hydrated lime.

Units equipped with fabric filters for particulate removal (baghouse units) do not experience ash resistivity; flue gas ash is removed by a bed established on the fabric. A more reactive hydrate will allow the end user to use less sorbent for similar effectiveness, or the opportunity to capture more acid species at equivalent sorbent use rates.

Calcination of hydrated lime in a boiler (Furnace Sorbent Injection, FSI) will form quicklime (CaO). This in situ generation of quicklime produces a sorbent that has more reactive surface area than can be provided by conventionally produced quicklimes or lime generated from fine limestone injection into the boiler. The quicklime generated in the boiler is a good sorbent for sulfur dioxide $SO_2$. The use of a higher reactive hydrated lime in FSI applications allows the Utility to use less hydrated lime to achieve similar reduction of $SO_2$. This is benefit in terms of downstream ash handling systems. There will also be reduced stress in process equipment due to slagging, backpass contamination. Conversely, the higher reactive hydrate can allow the end user to take advantage of higher removal rates using sorbent feed rates equivalent to standard hydrate. Reduced $SO_2$ emissions are an environmental benefit. Simple FSI systems also allow Utilities a low capital option for scrubbing compared to other options such as spray dry absorbers, wet FGD, or circulating dry scrubbers.

While this disclosure is not intended to be limited to any particularly theory of operation it is believed that small—but particularly more uniform as opposed to just smaller—particle size increases the probability of inter-particle collisions between the lime hydrate sorbent and the acid gas in the flue gas. And this in turn improves its effectiveness in reaction (due to higher "effective contact area"), particularly in applications where the exposure time is small. Further, to size prior to introduction to the hydrator and preparation of lime hydrate, but is milled after preparation. In alternative embodiments, the quicklime is milled to size prior to hydration. Further, the types of lime mills that exist are numerous. In an embodiment, it is generally preferred that the lime be milled, in one embodiment at all milling steps, but in others in at least the last milling step, utilizing a hammer, rotary, or tower mill as opposed utilizing a ball mill.

While Applicants do not intend to be bound by any one theory of operation, it is believed that a ball mill, when operating on lime that is sufficiently small, produces agglomerates of the material and actually will serve to increase the presence of larger particles, even while the mean particle size (d50) remains relatively small. That is, long exposure to a ball mill may reduce the d50 size, but increase the d90 and d90/d10 ratios. Table 1 shows two different hydrates, a high reactive hydrate produced using a hammer mill, and a standard hydrate produced using a ball mill.

TABLE 1

| Sample ID | Citric Acid Reactivity | Available Ca(OH)2 | Total Pore Volume | D50 | Steepness | D90 | D10 |
|---|---|---|---|---|---|---|---|
| High Reactive Hydrate | 3 | 95.56 | 0.0921 | 1.61 | 6.06 | 4.18 | 0.69 |
| Ball Milled Hydrate | 102 | 93.29 | 0.0849 | 1.52 | 11.23 | 7.53 | 0.67 | maintaining a reasonably high BET (above 18 $m^2/g$ or more preferably above 20 $m^2/g$) insures that average particle sizes do not lose their sorbent ability because of being overly small (if production of such small particles is even commercially feasible), or of having had their structure damaged through over-milling.

One of the concerns in manufacturing of particularly fine powders of lime hydrate is that the reactivity of the powder with acid gas is still believed, at least somewhat, to be dependent on the structural shape of the individual particles. If milled too finely, or using particular methods of milling, the average size and ratio of sizes may become sufficiently small, but the structure may be damaged as a result. Specifically, pores may become closed through action of the milling process. Thus, milling procedures which result in a decreased pore volume are generally less preferred over those that result in a higher pore volume. While it is generally expected that any milling technique could be used which produces lime hydrates meeting all three of the above discussed criteria—and/or being sufficiently reactive to citric acid to be considered high reactive lime hydrates—certain methods do appear to produce these types of materials more efficiently.

Applicants believe that the most effective manufacturing techniques for producing particles in the ranges above result from utilizing standard milling techniques to produce standard sized quicklime or lime hydrate products as are known to those of ordinary skill, and then to use particle segregation techniques to remove larger (and/or smaller) particles from the hydrate until a composition within the desired ranges or citric acid reactivity is obtained. This is believed to produce a higher quality product without significantly increased time and costs of production and can allow for rework of larger product to improve cost savings.

Lime milling operations and the creation of lime hydrate are generally understood by those of ordinary skill in the art. However, in some operations, lime is not specifically milled As can be seen from Table 1, the high reactive hydrate meets the desired criteria, however the ball milled sample, produced from the same feedstock, while showing a comparable d50 and d10, shows a massive increase in d90 (and correspondingly d90/d10 ratio). While Applicants do not intend to be bound by any one theory of operation, this is generally believed to be due to the loss of pore volume created by milling lime to such small sizes in a ball mill compared to other milling techniques and by the formation of agglomerates in the ball milling process.

Figure 9:
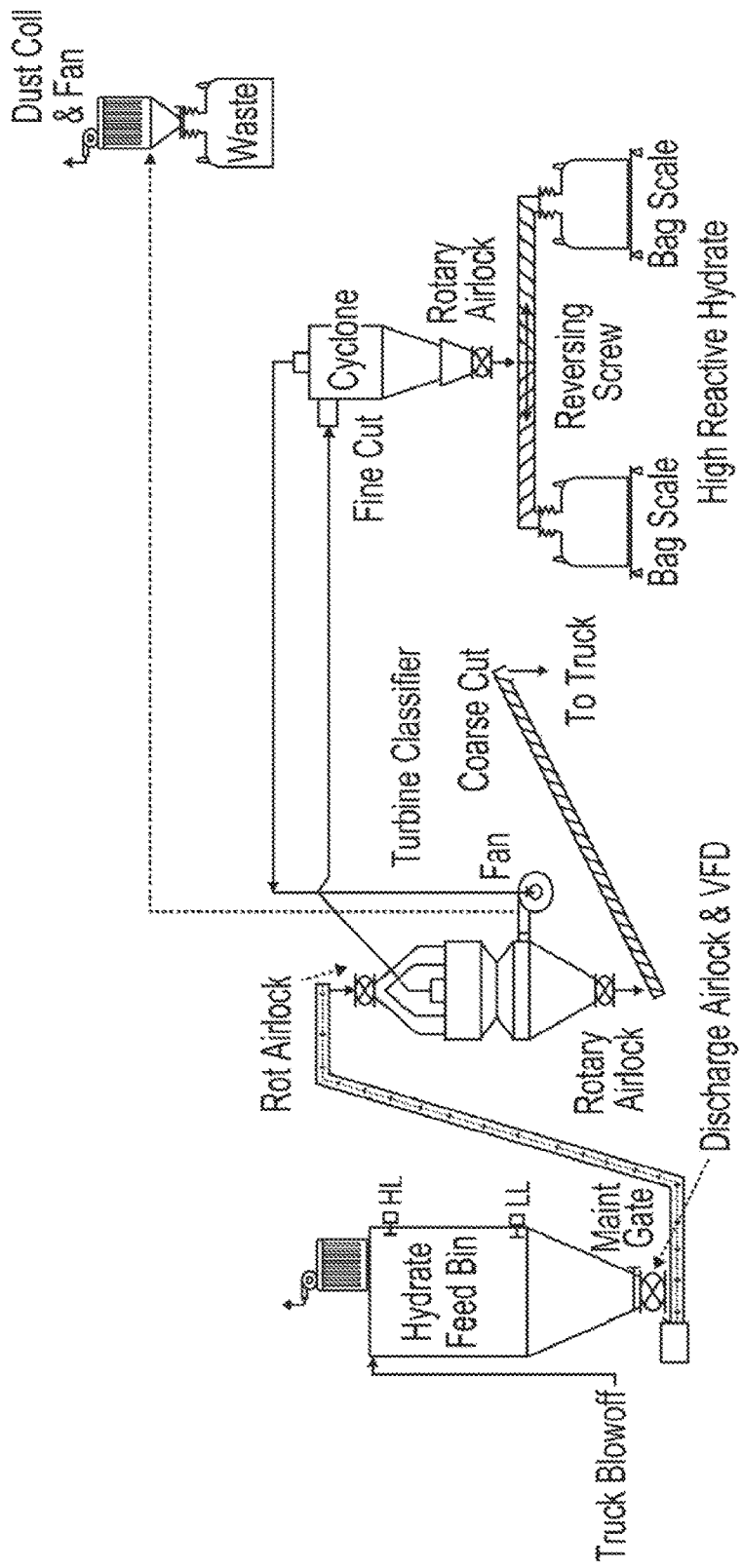
FIG. 9 shows a block diagram of an embodiment of an air classification separator setup.

While, in an embodiment, product can simply be milled until the desired d90 and d90/d10 are achieved (so long as the BET remains sufficiently high), this is generally not preferred as it can be very inefficient and take a lot of time. Instead, it is generally preferred that the feed quicklime be milled to standard sizes and grades. It then be formed into hydrate and a separator, such as, but not limited to an air classification separator as shown in FIG. 9, and then applied to this standard grade material to separate out the large components. The remaining smaller components are then evaluated against the ranges discussed above to determine if the resultant captured material meets all three ranges. This allows for amalgamates that may be formed in the hydrator to be removed prior to the final product being classified.

In the event that the final material does meet the three ranges, the material is then packaged in the standard fashion for sale or delivery. The larger particles which were removed may be separately sold for different applications, or may be fed back into a mill operating on lime hydrates as part of new feedstock for further milling.

Instead of determining if the selected material meets the three ranges, a separated material may instead be tested for citric acid reactivity and maintained regardless of its size characteristics, if it meets the desired citric acid reactivity. It is important to recognize, though, that given sufficient time, all lime hydrate will eventually react with available acid gas until one supply is exhausted. However, particularly in the flue gas scrubber and similar applications, the reaction time available for the reaction to be performed before the gas moves on is specifically limited by the fact that the flue gas is being continuously created and exhausted. Thus, the specific ability to neutralize flue gas over time, while necessary, is not as important of a consideration as the speed in which a large percentage of the neutralization occurs. Further, this speed requirement is generally very short (with the reaction having to occur within a couple seconds of exposure, and ideally within fractions of a second).

Figure 2:
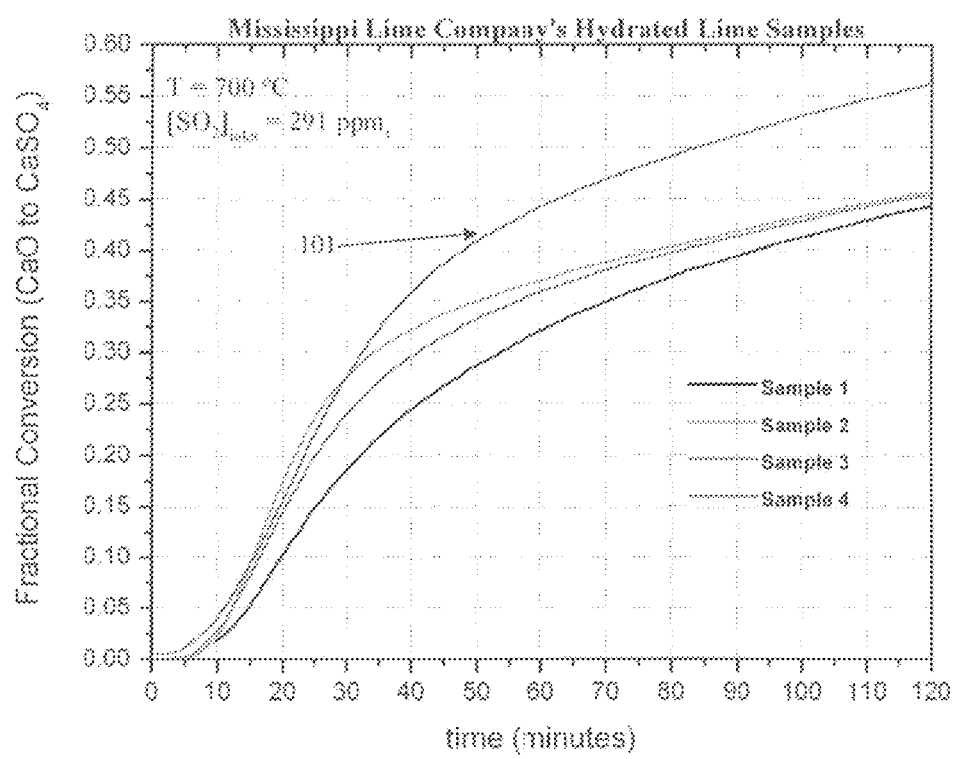
FIG. 2 provides a graph showing the reactivity of a high reactive hydrate (sample 3) in a standard test for Sulfur Dioxide ($SO_2$) neutralization along with three different standard hydrates.
Figure 3:
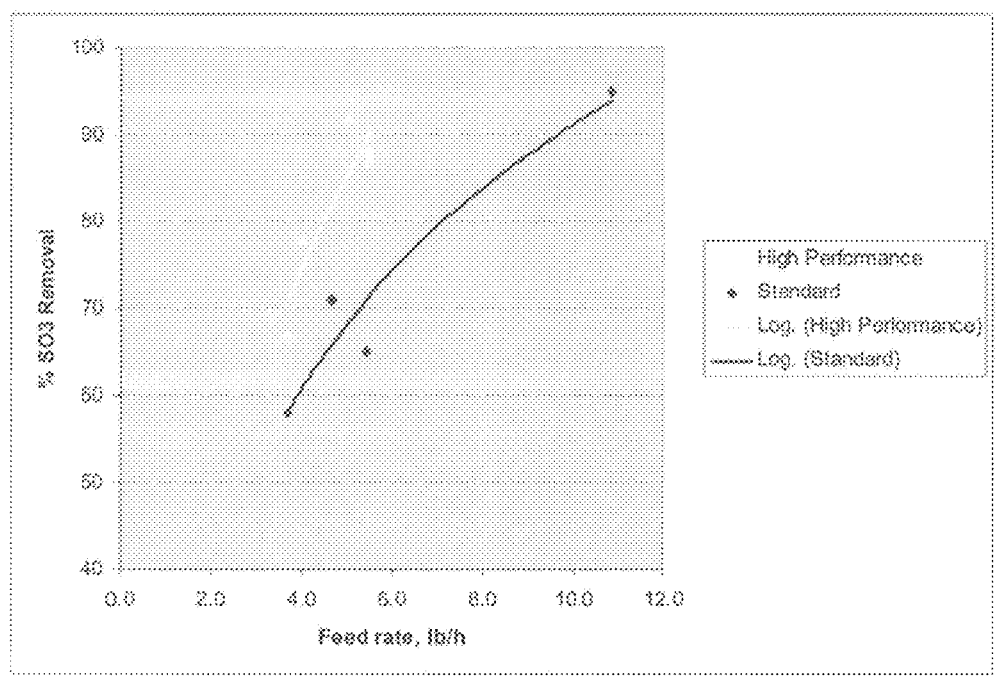
FIG. 3 provides a graph showing the effect of feed rate on $SO_3$ removal for standard and high reactivity hydrate.
Figure 4:
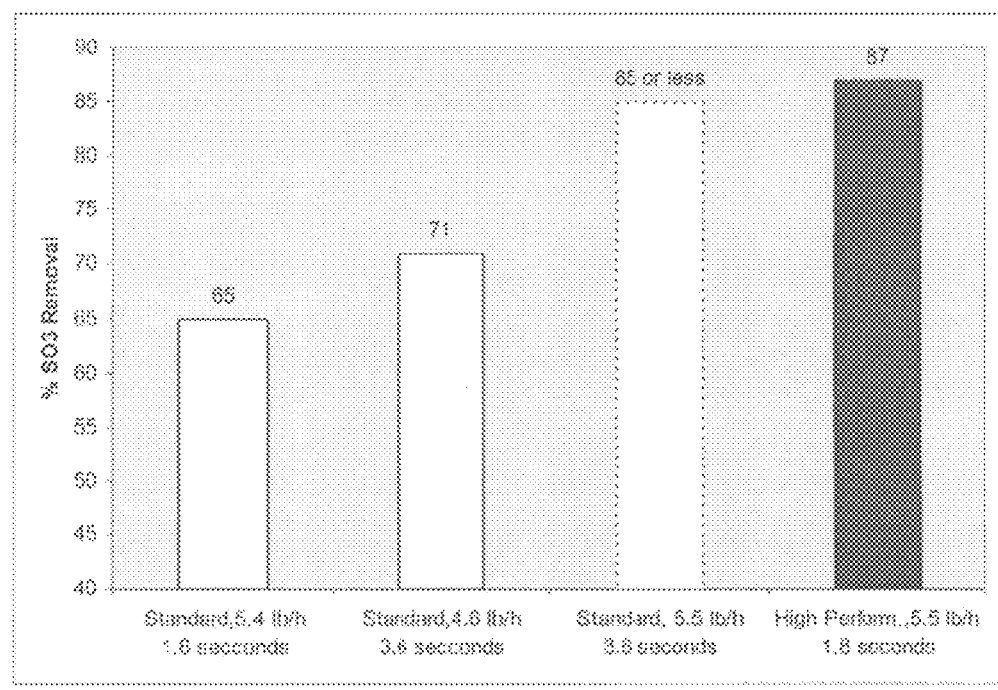
FIG. 4 provides a graph showing the effect of residence time on $SO_3$ removal for standard and high reactivity hydrate.

Prior to now, there have been no effective methods for determining reactivity time or the speed at which any particular amount of a particular sorbent can react with acid gas. Instead, different amounts of sorbent compounds were simply experimentally tested in flue gas processes (as contemplated by FIG. 2) to determine which was more effective at acid gas removal based on prior experience. While this can provide commercially viable solutions to the removal of acid gas from flue gas, it does not really provide for any method for determining if a particular composition would be more or less effective. Instead, it simply allows the operator to alter the amount or type of material used until the end result reaches a target. As can be seen in FIGS. 3 and 4, a high reactivity hydrate outperformed standard hydrates at a variety of feed rates and residence times showing that such end result control is still obtainable, while the high reactivity sample reacts more effectively in all cases. Another component of the present disclosure is directed to a method of testing a particular lime hydrate composition for effectiveness in a lab simulation, so that particularly effective compositions (such as those discussed above) can be utilized instead of using less effective materials in greater quantities.

In order to test reactivity of particular lime hydrate compounds, in an embodiment, the reactivity to a weak acid (such as, but not limited to, citric acid) provides for a reactivity time that is measurable with commercial instruments. The problem with determining reaction time to stronger acids is that the reaction can be too quick to effectively measure at laboratory scaling. Thus, it is difficult to predict compositions that will function well without performing large scale pilot testing. In order to determine the citric acid reactivity of a particular lime hydrate composition, the amount of time it took 1.7 g of lime hydrate to neutralize 26 grams of citric acid (as discussed more fully in Example 1) was taken. As a measurement of effectiveness, it is preferred that this value be less than or equal to 10 seconds in order to have a lime hydrate composition which is classified as being "high reactive". However, in an alternative embodiment it can be less than 8 seconds. It is more preferred that this value be 4 or less, 3 or less, 2 or less or 1 or less. Again, given the practical realities that production of improved material often results in a product having dramatically increased costs of products, utilizing current manufacturing techniques and for current emissions standards, in an embodiment the lime hydrate may be in the 2-5 second range, or, in another embodiment, in the 3-4 second range.

Figure 5:
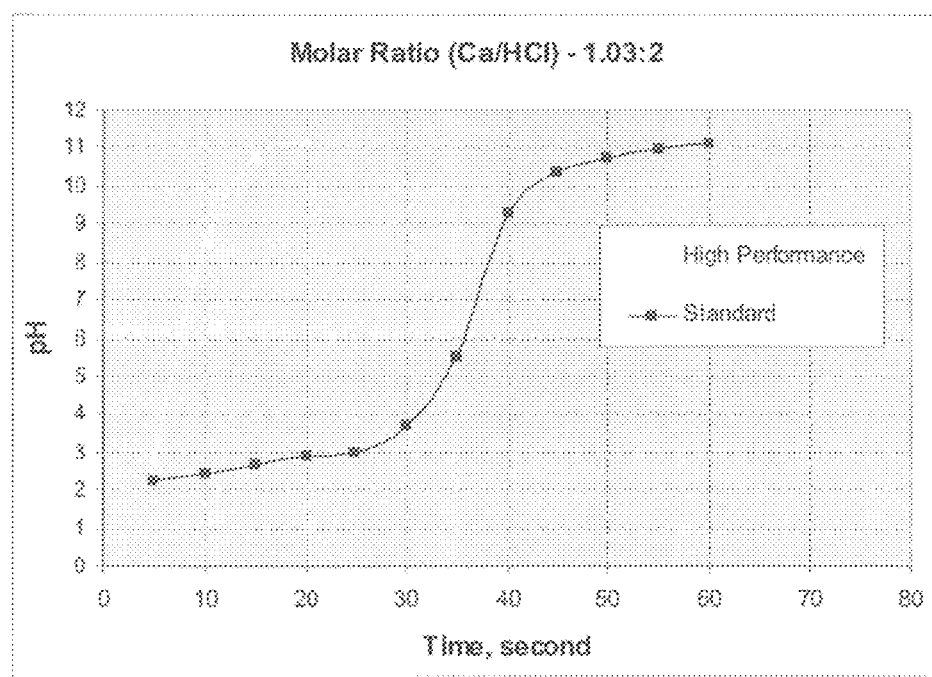
FIG. 5 provides a graph showing the relative neutralization speed of HCl for a standard and a high reactivity hydrate.
Figure 6:
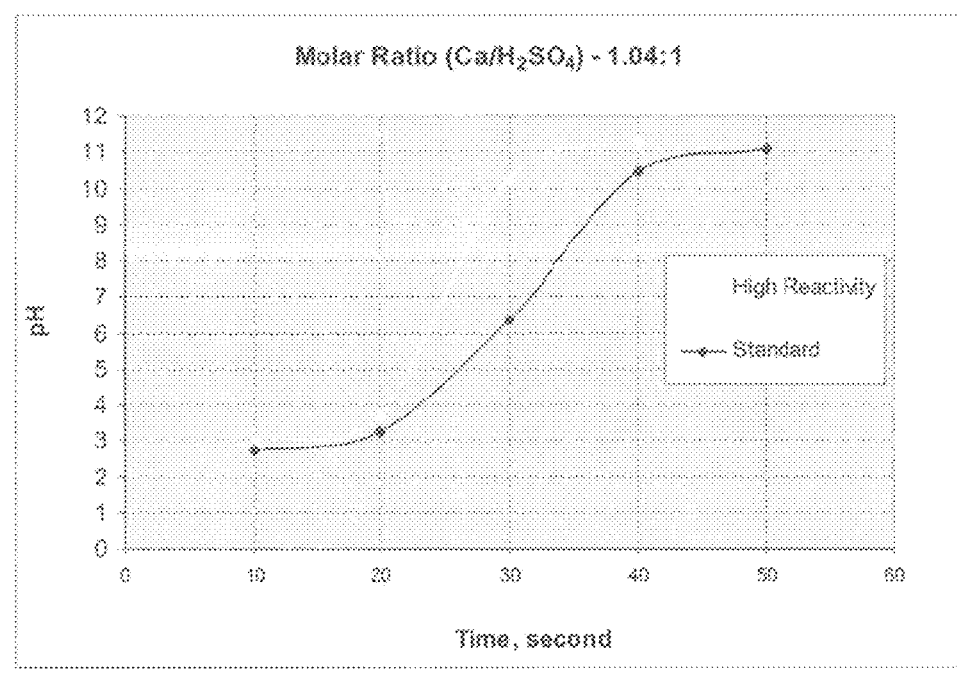
FIG. 6 provides a graph showing the relative neutralization speed of $SO_3$ for a standard and a high reactivity hydrate.

Without being limited to any particular theory of operation, it is also believed that the reactivity speed of a lime hydrate to citric acid is proportional to its reactivity with any acid gas. Thus, a lime hydrate having higher speed reactivity to citric acid will also have higher speed reactivity to acid gases. This theory is supported by FIG. 2 where a sample (101) of a high reactive gas (as indicated in Table 2 based on its citric acid reactivity) is compared against 3 low reactive samples (also in Table 2 based on citric acid reactivity) in a standard test for determining flue gas scrubbing effectiveness by determining uptake of Sulfur Dioxide ($SO_2$) over time. As can be seen in FIG. 2, the high reactive gas sample 3 (101) shows good initial uptake on par with known lime hydrates produced for scrubbing, but shows significantly improved uptake over time indicating improved performance against an acid gas. Similarly, FIGS. 5 and 6 show similar reactivity speed differences on HCl and $SO_3$. Thus, in an embodiment, there is also provided herein a lime hydrate composition which is capable of neutralizing about 10 times its weight in citric acid in a time of 10 seconds or less. Two examples of such a high reactive lime hydrate are provided in Table 2.

Table 2 provides for a comparison of a variety of different lime hydrate compositions. High Reactive Hydrates 1 and 2 are both examples of hydrates within the above range criteria. That is, having a BET greater than or equal to about 18 $m^2/g$, d90 less than or equal to about 6 microns, and d90/d10 less than or equal to about 8. As can be seen, the High Reactive Hydrates have significantly lower citric acid reactivity times indicating that they are highly reactive. The remaining compositions (indicated as Standard Hydrates 1-9 which comprise other commercially available hydrates and certain lab test samples) all show dramatically higher times of citric acid reactivity. However, as can be seen from the chart, many of these compounds score dramatically better in one or two of the ranges than the high reactive lime hydrate, but fail in the third, resulting in a compound which does not meet all three range criteria as contemplated above. For example, Standard Hydrate 8 has an incredibly high BET surface area and pore volume, which by conventional wisdom should perform well, but is one of the worst performers with a d90 and d90/d10 ratio well outside the ranges of this disclosure. Similarly, standard hydrate 1 has a d90 size and BET surface area within the above criteria, but lacks the narrowness of the d90/d10 ratio, and has a citric acid reactivity significantly worse than materials of comparable d90 size and BET surface area, but with size ratios in the above range.

TABLE 2

|  | Citric Acid Reactivity (seconds) | B.E.T. Surface Area ($m^2/g$) | Pore Volume | d 50 | Steepness ($D_{90}/D_{10}$) | D90 | D10 |
| --- | --- | --- | --- | --- | --- | --- | --- |
| High Reactive Hydrate 1 | 3 | 21.28 | 0.0833 | 1.76 | 5.72 | 4.12 | 0.72 |
| High Reactive Hydrate 2 | 4 | 21.27 | 0.0965 | 1.72 | 6.00 | 4.26 | 0.71 |
| Standard Hydrate 1 | 14 | 20.1 | 0.0770 | 1.92 | 6.21 | 4.66 | 0.75 |
| Standard Hydrate 2 | 13 | 16.64 | 0.0737 | 2.02 | 6.23 | 7.86 | 0.78 |
| Standard Hydrate 3 | 110 | 23.98 | 0.1115 | 1.8 | 8.86 | 6.56 | 0.74 |
| Standard Hydrate 4 | 102 | 21.17 | 0.0849 | 1.52 | 11.24 | 7.53 | 0.67 |

TABLE 2-continued

|  | Citric Acid Reactivity (seconds) | B.E.T. Surface Area (m²/g) | Pore Volume | d 50 | Steepness ($D_{90}/D_{10}$) | D90 | D10 |
|---|---|---|---|---|---|---|---|
| Standard Hydrate 5 | 27 | 21.46 | 0.0888 | 1.78 | 12.84 | 9.19 | 0.71 |
| Standard Hydrate 6 | 37 | 22.26 | 0.0952 | 1.56 | 14.52 | 9.73 | 0.67 |
| Standard Hydrate 7 | 58 | 25.53 | 0.0974 | 1.69 | 53.29 | 42.63 | 0.8 |
| Standard Hydrate 8 | 63 | 31.51 | 0.1268 | 10.73 | 60.33 | 54.9 | 0.91 |
| Standard Hydrate 9 | 12 | 17 |  | 1.83 | 6.49 | 4.47 | 0.73 |

While Applicants believe that preferred materials will meet all the above three criteria for particle size, steepness, and BET surface area of the lime hydrate composition, they believe that steepness is the most telling ratio and thus that compositions with sufficient steepness (for example a d90/d10 ratio under 4 or 3) may be able to meet the criteria of citric acid reactivity even with particle sizes outside the given range and/or BET surface areas outside the given range. However, it is generally expected that lowering at least one of BET surface area and particle size, while having a particularly low d90/d10 ratio will still produce a product with reduced citric acid reaction time and therefore in an embodiment, one can produce a high reactive lime hydrate by having a lime hydrate with at least two of the criteria (with one of the two being steepness) in the indicated ranges.

Example 1 provides an embodiment of a methodology for performing the test procedures used to determine the citric acid reactivity values shown in Table 2.

Example 1

This example provides a procedure to measure the reactivity rate of hydrated lime by measuring the amount of time required to neutralize a weak organic acid (specifically citric acid) to a given pH using a phenolphthalein indicator. The time taken for the Ca(OH)2 to neutralize a citric acid solution to the phenolphthalein color change is then termed "Hydrate Reactivity in Citric Acid."

In a 5 gallon vessel, mix 4.2 grams of phenol powder into 9338 ml of methyl alcohol. Add 4658 ml of DI water. Mix with air lance at low pressure to ensure a good mix.

Citric Acid/Indicator Solution: In a 1500 ml flask dissolve 26.0 g of "analytical reagent" grade citric acid (Taylor Scientific catalogue #C7410-1) in 500 ml of de-ionized water. Add 3 to 5 ml of phenolphthalein indicator and add DI water to make up a 1000 ml acid/indicator solution. Place stopper on flask and invert 5 times to mix solution.

Place 1.7 g of selected hydrate in a 600 ml beaker with a stir bar.

Turn on magnetic stirrer to the lowest setting.

Add 100 ml 72° F. (room temperature) de-ionized water.

Adjust stirrer speed to "high" speed and hold for 20 seconds using a stopwatch. The high speed setting was achieved by keeping an eye on the hydrate and water mixture to create a good vortex and not have any of the hydrate solution splash out, or have the stir bar "freak out" and start bouncing around. On a scale of 1 to 10, with 10 being high, this is an 8 setting on the Thermolyne Cimarec 2 magnetic stirrer in use in the White Lime II lab.

After 20 seconds stop the stopwatch, reset it, and adjust the stirrer to a medium speed. Again the goal is to maintain a good vortex and not splash out the hydrate/water solution during acid addition. This is a 6 speed setting on the W.L. II lab stirrer.

Add 100 ml 72° F. citric acid solution. In a 1500 ml flask dissolve 26 g of "analytical agent" grade citric acid in 500 ml de-ionized water. Add 5 ml of phenolphthalein and dilute with D.I. water to 1000 ml mark. Place a stopper on the flask and invert 5 times to mix.

Restart the stopwatch as soon as the acid hits the hydrate solution.

Adjust the stirrer speed to the high setting.

Stop the stopwatch when pink color appears.

Example 2

Example 2 discusses a pilot trial that was run at a small, coal fired boiler. This boiler is used for evaluative purposes of numerous emission control scenarios. The boiler and emission control system is designed and operated to duplicate the respective temperature and time profiles of a full scale Utility boiler. In Example 2, various forms of hydrated lime were tested for removal capability of $SO_3$ in the flue gas. For each hydrated lime tested, a controlled amount of hydrated lime was added to the flue gas prior to particulate collection. The capability of each hydrate to remove a predetermined amount of $SO_3$ was determined and compared. FIG. 3 shows the effect of sorbent feed rate on the $SO_3$ removal for standard hydrate and high performance hydrate, respectively. $SO_3$ removal increases with increasing feed amount of the respective hydrated limes. However, at a given feed rate, the high performance hydrate allows significantly more reduction of $SO_3$ than the standard hydrate. In a situation when a targeted rate of $SO_3$ removal is defined (such as 90%), the sorbent feed rate required is considerably lower for the higher performance hydrate compared to standard hydrated lime. This represents potential cost savings to the end users.

FIG. 4 shows the effect of residence time on $SO_3$ removal. Residence time plays a critical role for effective acid gas removal. In the example shown by FIG. 4, standard hydrate gave 65% $SO_3$ reduction (at a feed rate of 5.4 lb/hr) when the sorbent injected at the location of 1.8 seconds residence time. Increasing the residence time to 3.6 seconds yielded an improved $SO_3$ removal of 71% for the standard hydrate, even with a reduced feed rate of 4.6 lb/hr. It is estimated that the $SO_3$ removal rate was about 85% or less when the feed rate was adjusted to the same, based on best linear estimation in FIG. 3. In contrast, the high performance hydrate gave 87% at the same feed rate but at a much lower residence time (1.8 sec). This is very significant in that the high performance hydrate is a solution when the choice of injection locations is limited at the end users' site.

Example 3

Example 3 discusses a full scale test of high reactive hydrated lime in a Utility boiler. Using conventional equipment for Dry Sorbent Injection, a Utility boiler firing bituminous coal and equipped with SCR, APH, ESP and wFGD for flue gas control used hydrated lime for control of $SO_3$ emissions. In the first test, a prescribed amount of hydrated lime was conveyed to the process and added after the APH. Using standardized wet chemical testing, the $SO_3$ emissions were reduced by 76% when standard hydrated lime was used. The following test utilized High Reactive hydrated lime and achieved a reduction in $SO_3$ content of 95% by the same wet chemical testing and using the same configuration and hydrated lime feed rate. The results are summarized in Table 3.

TABLE 3

| Day 1 | | | | | |
|---|---|---|---|---|---|
| SO3 content baseline | | | SO3 content with Hydrate Treatment | | |
| Run | Sampling Time | SO3 ppm @ 3% | Run | Sampling Time | SO3 ppm @ 3% |
| AVERAGE | | 33.5 | AVERAGE | | 7.9 |
| Day 2 | | | | | |
| SO3 content baseline | | | SO3 content with High Reactive Hydrate Treatment | | |
| Run | Sampling Time | SO3 ppm @ 3% | Run | Sampling Time | SO3 ppm @ 3% |
| AVERAGE | | 27.0 | AVERAGE | | 1.3 |

$SO_3$ was calculated by the controlled condensation method.

Example 4

Example 4 was a small scale evaluation of high temperature removal of $SO_2$ using hydrated lime. The test process heated hydrated lime past dehydration to form calcium oxide in a controlled atmosphere. This calcium oxide reacts with sulfur dioxide in the test apparatus to form calcium sulfate. The results of the test comparison are provided in FIG. 2, where Sample 3 is the high performance hydrated lime and samples 1, 2, and 4 are standard hydrated limes of differing origin. Using this standardized lab scale process, the high performance hydrate exhibited a capacity to absorb 30% more $SO_2$ than standard hydrated limes.

While the invention has been disclosed in conjunction with a description of certain embodiments, including those that are currently believed to be the preferred embodiments, the detailed description is intended to be illustrative and should not be understood to limit the scope of the present disclosure. As would be understood by one of ordinary skill in the art, embodiments other than those described in detail herein are encompassed by the present invention. Modifications and variations of the described embodiments may be made without departing from the spirit and scope of the invention.

It will further be understood that any of the ranges, values, or characteristics given for any single component of the present disclosure can be used interchangeably with any ranges, values or characteristics given for any of the other components of the disclosure, where compatible, to form an embodiment having defined values for each of the components, as given herein throughout. Further, ranges provided for a genus or a category can also be applied to species within the genus or members of the category unless otherwise noted.

The invention claimed is:

1. A method of determining the relative acid gas reactivity of sorbents, the method comprising:
   providing a first sample including calcium hydroxide particles;
   exposing said first sample to a first predetermined amount of citric acid, said first predetermined amount of citric acid having a selected mass greater than 10 times the mass of said calcium hydroxide particles in said first sample;
   determining an amount of time it takes said first sample to completely neutralize in said first predetermined amount of citric acid;
   providing a second sample including calcium hydroxide particles;
   exposing said second sample to a second predetermined amount of citric acid, said second predetermined amount of citric acid having a selected mass greater than 10 times the mass of said calcium hydroxide particles in said second sample;
   determining an amount of time it takes said second sample to completely neutralize in said second predetermined amount of citric acid;
   comparing said amount of time for said first sample to completely neutralize in said first predetermined amount of citric acid to said amount of time for said second sample to completely neutralize in said second predetermined amount of citric acid;
   wherein a ratio of said mass of said calcium hydroxide particles in said first sample to said mass of said first predetermined amount of citric acid is about the same as a ratio of said mass of said calcium hydroxide particles in said second sample to said mass of said second predetermined amount of citric acid.

2. The method of claim 1 wherein at least one of said first sample and said second sample is completely neutralized in less than 10 seconds.

3. The method of claim 1 wherein at least one of said first sample and said second sample is completely neutralized in less than 8 seconds.

4. The method of claim 1 wherein at least one of said first sample and said second sample is completely neutralized in less than 4 seconds.

5. The method of claim 1 wherein at least one of said first sample and said second sample is completely neutralized in less than 3 seconds.

6. The method of claim 1 wherein at least one of said first sample and said second sample is completely neutralized in between about 2 seconds and about 5 seconds.

* * * * *